United States Patent [19]

Virsu et al.

[11] Patent Number: 5,746,205
[45] Date of Patent: May 5, 1998

[54] METHOD AND APPARATUS FOR MEASURING THE WORKING CONDITION OF THE BRAIN WITH PERIODIC STIMULI

[75] Inventors: Veijo Virsu, Espoo; Seppo Salminen, Helsinki, both of Finland

[73] Assignee: Helsinki University Licensing, Ltd., Helsinki, Finland

[21] Appl. No.: 609,682

[22] Filed: Mar. 1, 1996

[51] Int. Cl.$^6$ .................................................. A61B 5/00
[52] U.S. Cl. .................. 128/630; 128/739; 128/740; 128/741; 128/742; 128/745; 128/746; 128/744
[58] Field of Search .................. 128/630, 732, 128/739–742, 744, 745, 746

[56] References Cited

U.S. PATENT DOCUMENTS

| | | | |
|---|---|---|---|
| 3,707,710 | 12/1972 | Adler et al. | 128/745 |
| 4,305,402 | 12/1981 | Katims | 128/741 |
| 4,892,106 | 1/1990 | Gleeson, III | 607/91 X |
| 5,522,386 | 6/1996 | Lerner | 128/630 |

FOREIGN PATENT DOCUMENTS

| 0673266 | 7/1979 | U.S.S.R. | 128/745 |
|---|---|---|---|

OTHER PUBLICATIONS

Gander et al., "Precise Stimulus for the measurement of visual flicker sensitivity" Rev. Sci. Instrum. 51(10) Oct. 1980.

Virsu et al., "Visual Resolution, Contrast Sensitivity, and the Cortical Magnification Factor", Experimental Brain Research pp. 475–494 (1979).

Treutwein, "Minireview–Adaptive Psychophysical Procedures", Vision Research, vol. 35 No. 17, pp. 2503–2522 (1995).

*Primary Examiner*—Jeffrey R. Jastrzab
*Attorney, Agent, or Firm*—Marshall, O'Toole, Gerstein, Murray & Borun

[57] ABSTRACT

The working quality of the human brain is measured with this method and apparatus by determining the highest frequency at which a subject can discriminate between synchronous and asynchronous pairs of two simultaneously presented periodic non-verbal stimuli: the higher this frequency (synchronism threshold) is the faster the brain of the subject can process information using the sensory function tested. The periodic stimuli provided to the subject and preceded by appropriate mask stimuli may be pairs of visual, tactile, electrocutaneous, and/or auditory stimuli within the same sense modality, or intermodal between two different senses. The apparatus generates the stimuli and indicates the nominal frequencies of the stimuli and threshold. The frequency threshold is determined by means of an adaptive staircase procedure in which the frequency is decreased after wrong responses and increased after correct responses.

28 Claims, 7 Drawing Sheets

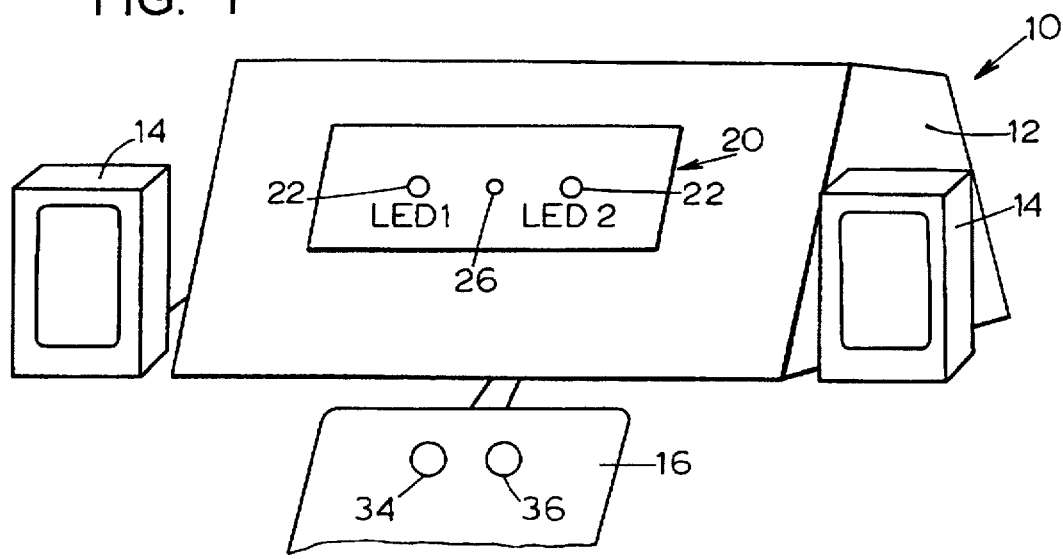
FIG. 1
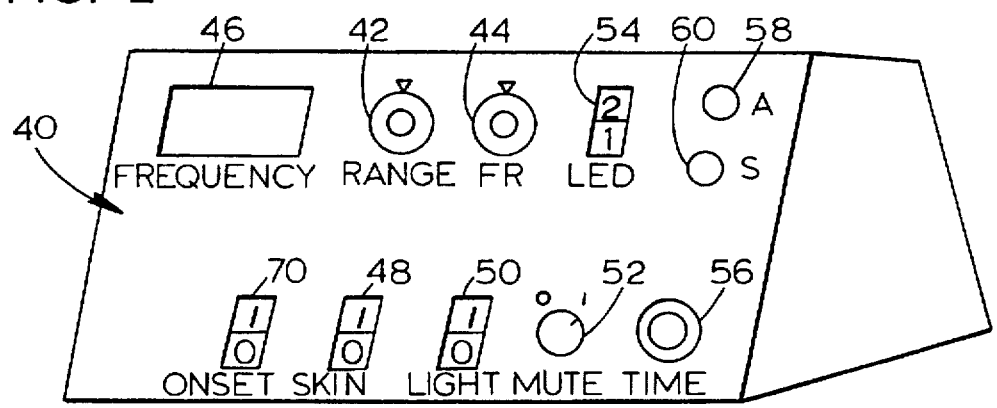
FIG. 2
FIG. 3A
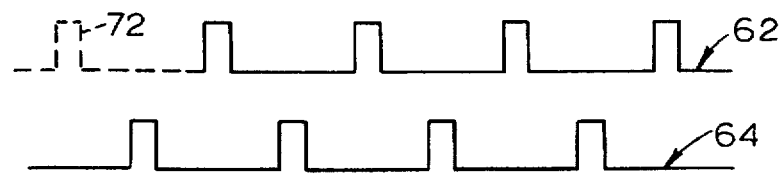
FIG. 3B
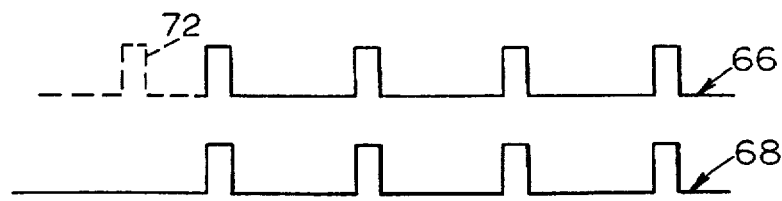

METHOD AND APPARATUS FOR MEASURING THE WORKING CONDITION OF THE BRAIN WITH PERIODIC STIMULI

BACKGROUND OF THE INVENTION

The invention relates to a method of measuring the working quality of the human brain using elementary non-verbal periodic stimuli simultaneously or separately for different senses, and an apparatus for generating the periodic stimuli and testing the information-processing capacities of the human brain using this method.

The general behavior-controlling quality and information-processing capacity of the human brain cannot be assessed reliably and easily with tests now in use. Intelligence and achievement tests have been used to measure the functional capacity of the brain, but they do so indirectly by relying on indicia of cognitive achievement. The results of psychological tests are so complicated also that they cannot be interpreted in neural terms. Neurological signs are crude and give behavioral information only in special cases. Recently developed functional imaging methods cannot predict normal behavioral capacities, give piecemeal information of the brain as a control system, and are expensive to use. The present method complements the earlier ones by filling the gap between the information given by neurological and psychological methods. The method gives new elementary behavioral information that can be compared with blood pressure and pulse rate measurements when examining the condition of the heart, while the information produced with existing methods for the quality of the brain can be compared to the information given by sport achievements or electrocardiogram for the heart.

The speed at which the brain processes information is a basic indicator of the working capacity of the brain, and may play a factor in determining one's memory, intelligence, and cognitive abilities: the faster a tested neural system works, the higher is its frequency threshold and the wider is its bandwidth. In general, cognitive processes and motor responses become slower with age after middle age. It has been concluded by J. Cerella that information-processing latencies taken from elderly subjects correspond, qualitatively and quantitatively, to those that would be expected from a brain whose neural interconnections were systematically disrupted or attenuated.

Slowing of the information processing speed of the brain causes asynchrony of mental processes because different neural pathways have different lengths and vulnerabilities. Many variations of reaction time or double-pulse tasks are in common use but the asynchrony cannot be measured with these methods because they are not repetitive to reveal the erasure effects that inhibition and buffering produce in the brain, and when complex stimuli and their sequences are used, results obtained with them are limited and disputable in neural interpretations, and none of these methods have been used to test synchrony between different sensory systems (intermodally). Temporal accuracy is however necessary for parallel processing in several neural structures, and accurate timing of signals may be necessary for other neural events. The new imaging methods have indicated that many neural pathways are simultaneously used at each stage in controlling the performance of a complex task, and temporally accurate cooperation can be as important for them as it is for the members of an orchestra. Because the pathways contain different numbers of consecutive neurons and because different types of neurons have different probabilities of deterioration, the latencies of different pathways may differ from each other. Therefore, in addition to slowing the information processing speed of the brain, the disruption of neural interconnections leads to asynchrony of brain processes that increases in seriousness when the complexity of the process increases.

The slowing of mental processes and increase of temporal dispersion is not caused solely by the loss or weakening of connections in itself, but also by the lack of effective organization in the neural connections available. In the elderly, the loss of neural connections causes detours and disorganization, which impedes and retards mental processes. In children, the early synaptic organization as a whole is largely non-functional, but the organization of the nervous system improves with age due to learning and development. If the effective organization of the control circuits of the brain is poor, many useless and confounding signals affect each neuron and decrease their signal-to-noise ratio. The highest signal frequency that can be discriminated correctly by a neural system depends on the signal-to-noise ratio. The temporal frequency threshold (the highest nominal frequency discriminated at a given probability of hits) for a subject, tapping the brain function tested, indicates then the shortest time interval that allows one signal to be processed separately from another in certain control system of the subject's brain.

SUMMARY OF THE INVENTION

The invention is to use the highest nominal frequency (the inverse of the shortest period length) at which a subject can detect asynchronism in periodic stimuli (synchronism threshold) as a measure of quality of the brain function tested. A subject's responses to elementary periodic stimuli of different frequencies may be used to generate an objective behavioral indication of the working quality of the subject's brain: the higher is the threshold frequency the faster and better the brain system tested can control the relevant action. The synchronism threshold is measured by determining the subject's ability to differentiate between synchronous and asynchronous periodic stimuli of various frequencies when several stimulus periods are presented. The periodic test stimuli can be preceded by variable mask stimuli when the experimenter wants to make sure that the subject's two-alternative forced-choice response takes place on the basis of synchronism/asynchronism of the periodic signals and not on the basis of some other irrelevant cue. Several different sense modalities, such as vision, hearing, and skin senses, can be tested singly and in combination (intermodally) in order to define the neural systems tested.

The invention is directed to a method of measuring the working quality of the brain of a subject with periodic stimuli and to an apparatus for use in the method. In the method, the subject is substantially simultaneously exposed to two periodic stimuli of which the first has a substantially constant frequency and the second stimulus a frequency substantially the same as the frequency of the first periodic stimulus. The periodic stimuli provided to the subject as pairs may be visual stimuli, tactile stimuli, electrocutaneous stimuli, and/or auditory stimuli, or any combination thereof. The two periodic stimuli simultaneously provided to the subject can be of different types, such as visual and tactile.

The first and second periodic stimuli are generated either synchronously or asynchronously substantially at half-period phase shifts, and the subject is tested to determine whether the first and second stimuli were perceived to be synchronous or asynchronous. Depending on whether the subject correctly described the synchronism of the first and second stimuli, the frequency at which the next pair of stimuli is generated is changed, and the subject is simultaneously exposed to third and fourth periodic stimuli at a new frequency. The third and fourth stimuli may be either synchronous or asynchronous.

In the method, the frequency at which subsequent periodic stimuli are generated may be increased in response to a predetermined number of correct indications given by the subject and decreased in response to a predetermined number of incorrect indications given by the subject, depending on the probability of hits desired for the threshold stimulus. The periodic stimuli may be generated until they exhibit a predetermined number of turning frequencies, each of which represents a frequency at which there was a directional frequency change. A synchronism threshold frequency, that is, the inverse of the shortest period length for the stimulus correctly perceived by the subject at a given probability, may be calculated by determining an average of a predetermined number of the turning frequencies.

The invention is also directed to an apparatus for generating the periodic stimuli, masking their onsets with preceding mask stimuli when considered necessary, and determining the synchronism thresholds. The apparatus includes first and second means for generating periodic stimuli to the subject, means for generating first and second periodic signals having a substantially constant frequency and transmitting the first and second periodic signals to the stimuli-generating means, switch means for selecting whether the first and second periodic signals are synchronous or asynchronous, and means for adjusting and reading the frequency at which the periodic signals are generated.

As in the method, the stimuli-generating means may generate visual stimuli, tactile stimuli, electrocutaneous stimuli, and/or auditory stimuli, or any combination thereof. The apparatus may also have indicating means for allowing the subject to make an indication as to whether the periodic stimuli were synchronous or asynchronous and means for calculating and recording a synchronism threshold of the subject based upon a plurality of indications made by the subject via the indicating means.

These and other features and advantages of the present invention will be apparent to those of ordinary skill in the art in view of the detailed description of the possible embodiment, which is made with reference to the drawings, a brief description of which is provided below.

BRIEF DESCRIPTION OF THE DRAWINGS

FIG. 1 is a perspective view of a first embodiment of a testing apparatus that generates periodic stimuli in accordance with the invention;

FIG. 2 is a perspective view of a control panel of the testing apparatus of FIG. 1;

FIG. 3A illustrates a pair of asynchronous waveforms generated during operation of the testing apparatus of FIG. 1;

FIG. 3B illustrates a pair of synchronous waveforms generated during operation of the testing apparatus of FIG. 1;

DETAILED DESCRIPTION OF A PREFERRED EMBODIMENT

Figure 4:
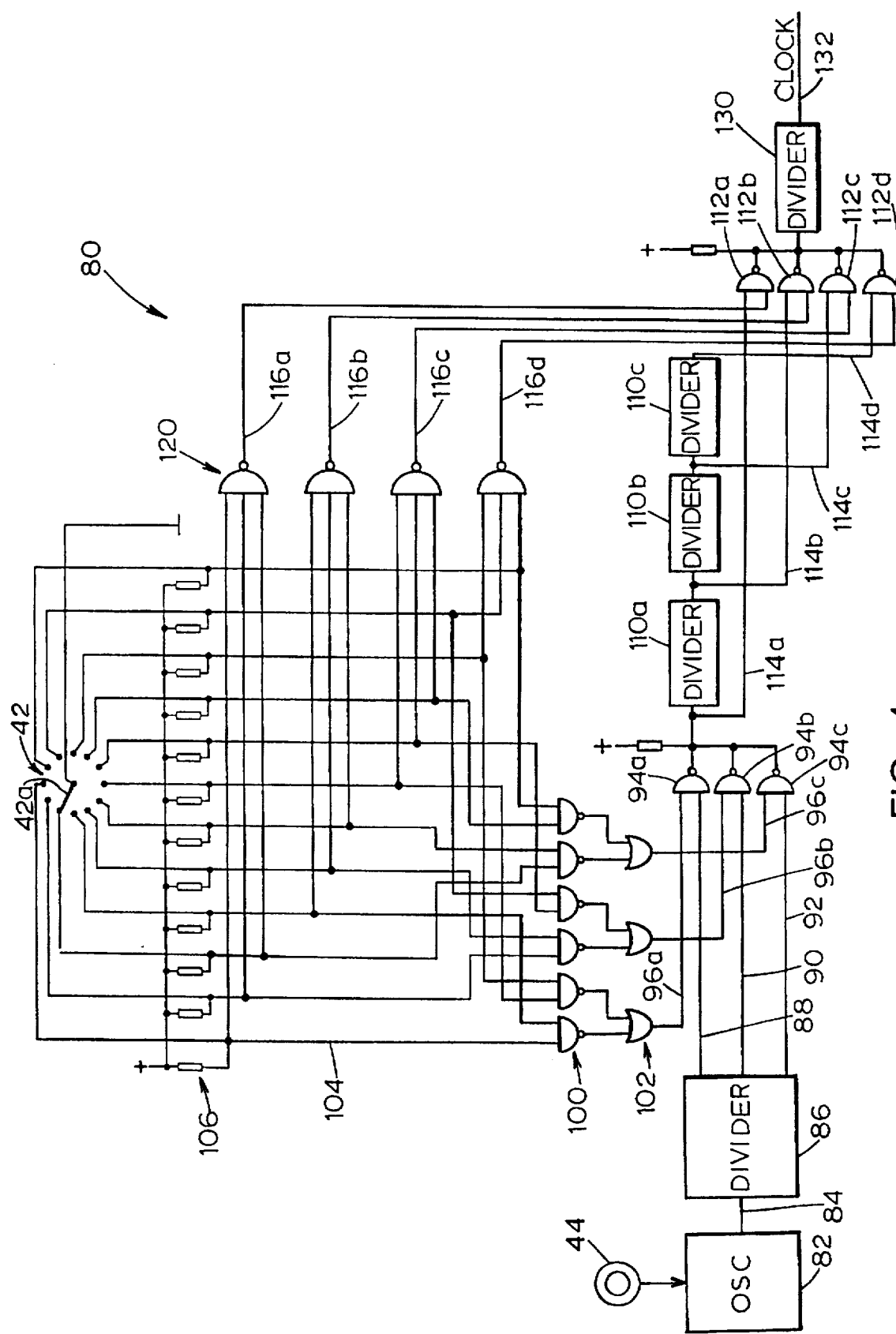
FIG. 4 is a circuit diagram of a frequency generating circuit of the testing apparatus.

FIG. 1 illustrates a first embodiment of a testing apparatus 10 for generating periodic stimuli for measuring the working quality of the brain of a living human subject. Referring to FIG. 1, the testing apparatus 10 includes a control module 12, a pair of audio speakers 14 for generating periodic auditory stimuli for the subject, and a touchpad 16 for generating tactile stimuli for the subject. The side of the testing apparatus 10 which faces the subject during testing includes a display portion 20 having right and left light-emitting diodes (LEDs) 22 and a central LED 26.

During testing of a subject, the right and left LEDs 22 may be periodically illuminated either synchronously or asynchronously for a certain stimulus presentation time or for a certain number of flash periods, and the central LED 26 is continuously illuminated to provide a visual reference point to the subject. When illuminated synchronously, the LEDs 22 turn on and off at the same time, and when illuminated asynchronously they are alternately illuminated. The highest frequency (the shortest time interval) at which the subject can indicate whether the LEDs 22 are being illuminated synchronously or asynchronously is indicative of the subject's visual sensory information processing capability. Terms "first" and "second", or "third" and "fourth" stimuli refer to the pair of periodic stimuli whose synchronism is assessed by the subject, like that of the two LEDs.

When the LEDs 22 are periodically illuminated at low frequencies, it is easy to detect whether they are illuminated synchronously or asynchronously; however, as the frequency of illumination increases, that determination is more difficult, and at high frequencies the determination can take place only at a chance level. The threshold frequency at which the subject can no longer detect the illumination mode is indicative of the subject's visual information processing capability, as described in more detail below. The audio speakers 14 can also be driven either synchronously or asynchronously at various frequencies to test the auditory response of the subject, and their stimuli can be presented synchronously or asynchronously with the light stimuli to test the visual/auditory intermodal processing capability. The audio speakers can be replaced with headphones having hearing protection.

Figure 6:
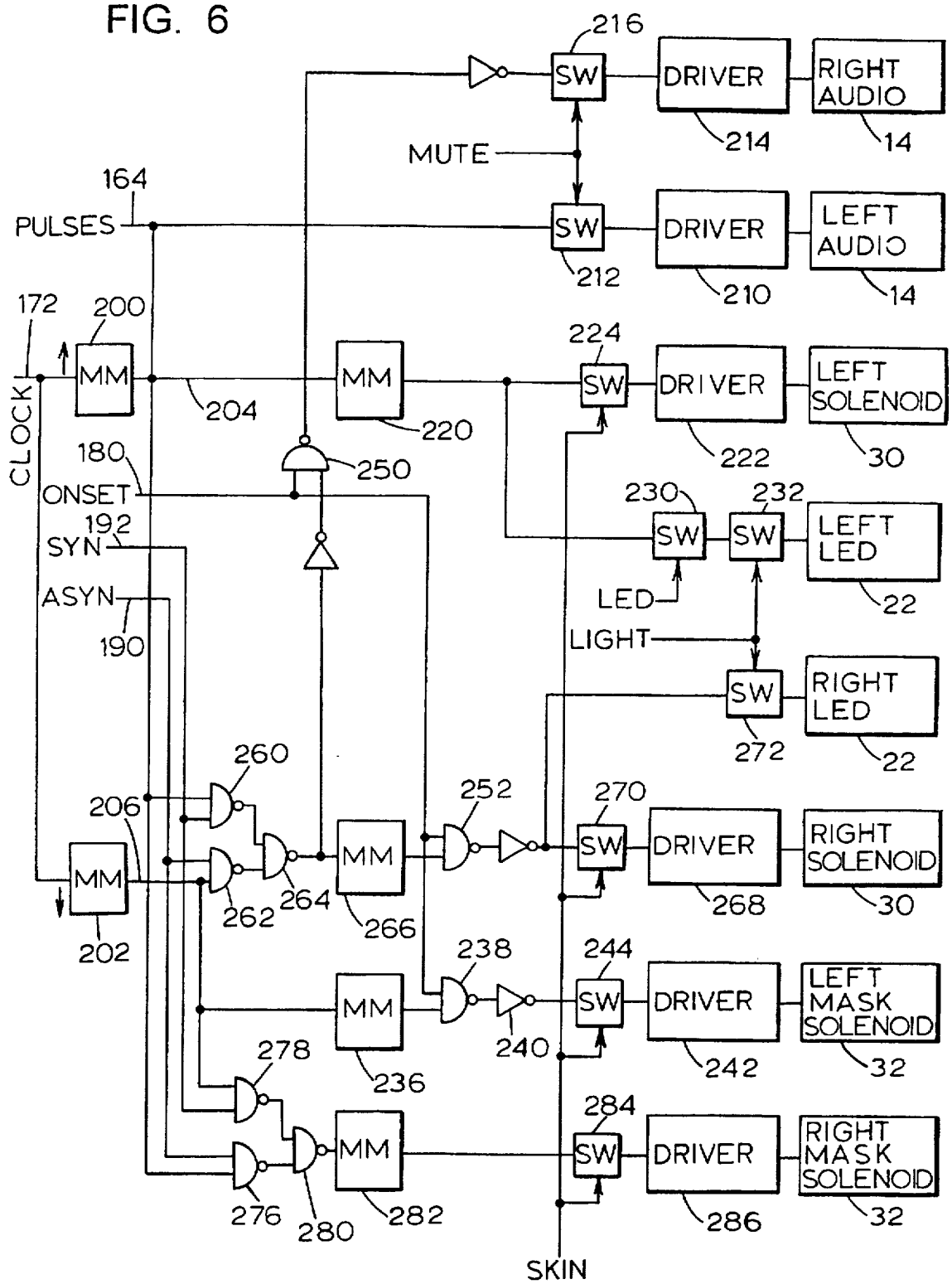
FIG. 6 is a circuit diagram of a second portion of the control circuit.

The touchpad 16, which is composed of a soft, thin material and intended to test the subject's response to synchronous and asynchronous tactile stimuli, has two solenoid boxes (not shown) disposed therein, each of which has a sensory solenoid 30 and a masking solenoid 32 (shown schematically in FIG. 6). Each sensory solenoid 30 is vertically displaceable between a pair of vertically offset positions located directly below one of a pair of differently colored circles 34, 36.

Like the LEDs 22 described above, the sensory solenoids 30 located beneath the circles 34, 36 may be driven synchronously or asynchronously at various frequencies, and one of them can be driven together with visual or auditory stimuli in order to test as pairs the tactile/visual or tactile/auditory intermodal processing capabilities. When driven synchronously, the two sensory solenoids 30 move up and down together, and when driven asynchronously they move in opposite directions. When being tested, the subject places a fingertip over each one of the colored circles 34, 36 and is requested to indicate whether the solenoids 30 are moving synchronously or asynchronously through the thin, soft material of the touchpad 16.

When driven, the sensory solenoids 30 generate a clicking sound each time they are activated. This sound as an auditory cue assists the subject in determining whether the solenoids 30 are being driven synchronously or asynchronously. Since the object of the sensory solenoids 30 is to test the tactile response of the subject, one of the masking solenoids 32 is provided adjacent the sensory solenoid 30 in each solenoid box so that the cumulative sound generated by all four solenoids 30, 32 is identical, regardless of whether the sensory solenoids 30 are being driven synchronously or asynchronously.

FIG. 2 illustrates a control panel 40 of the testing apparatus 10, which is located on the side opposite the side having the display panel 20. The control panel 40, which is used by the operator of the testing apparatus 10, has a frequency range select switch 42 that may be set to any one of twelve different frequency ranges to control the frequency at which any of the stimuli-generating devices 14, 22, 30 are driven. A frequency adjust switch 44 may be rotated to provide adjustment of the frequency selected by the frequency range switch 42. The frequency that is specified by the combination of the settings of the switches 42, 44 may be displayed visually in a frequency display 46.

The testing apparatus 10 allows the operator to select one or more of the three stimulus modes described above during testing of a subject. To that end, the control panel 40 has a two-position toggle switch 48 (position "1" for activating the solenoids 30, 32; position "0" for deactivating them) that determines whether the solenoids 30, 32 are driven during a test sequence, a toggle switch 50 that determines whether the LEDs 22 are illuminated during a test sequence, and a muting switch 52 that determines whether the audio speakers 14 are driven during a test sequence. A two-position toggle switch 54 (position "2" activating both LEDs 22; position "1" activating only the right LED 22) is provided to allow the operator to illuminate only one of the LEDs 22 and producing a synchronous sound during a test.

The time duration of the periodic stimuli presented to the subject may be selected by a rotary switch 56, which has four positions which specify different time periods, e.g. one second, two seconds, four seconds, eight seconds, and six positions which specify the number of pulses which are transmitted during a periodic stimulus, e.g. one, two, four, 16, 64, or 256 flash pairs in the LEDs 22 or click pairs in the audio stimulator 14.

The control panel 40 includes an asynchronous-stimulus start button 58 and a synchronous-stimulus start button 60. When the asynchronous start button 58 is pressed, the testing apparatus 10 transmits a pair of asynchronous periodic signals having the shape shown generally as waveforms 62, 64 in FIG. 3A. The periodic signals, which have the frequency selected by the switches 42, 44, drive the stimuli generators 14, 22, 30 selected by the switches 48, 50, 52, 54 and are transmitted for the duration specified by the switch 56. When the synchronous start button 60 is pressed, the testing apparatus 10 transmits pair of synchronous periodic signals having the shape shown generally as waveforms 66, 68 in FIG. 3B. At threshold frequencies the two stimuli are substantially simultaneous even when they are asynchronous.

A two-position toggle switch 70 may be used to select whether or not an onset mask pulse is transmitted with the periodic stimuli. An onset mask pulse is a single pulse which is added to the beginning of both periodic test signals to make it more difficult for the subject to distinguish synchronous stimuli from asynchronous test stimuli based only on the initial portion of the periodic stimuli. Referring to FIGS. 3A and 3B, an onset pulse 72, shown in dotted lines, is added to the start of both pairs of test signals so that they always start asynchronously and do not indicate whether the periodic test stimulus pair is synchronous or not. The interval with which the mask pulse precedes the periodic stimulus varies according to the clock status of the apparatus and depends on how fast the operator lifts a finger from a start button 58 or 60. Thus, the mask pulse intervals are variable and substantially random from the point of view of the subject.

To test a subject, the operator of the testing apparatus 10 first selects one or more stimuli modes via the switches 48, 50, 52, 54 and the desired time duration of the stimuli via the switch 56. The operator then selects a starting frequency, via the switches 42, 44, that the operator believes is relatively close to the threshold at which the subject can distinguish between asynchronous and synchronous stimuli.

The operator then initiates a pair of stimuli at the starting frequency by pushing one of the buttons 58, 60 at random. After the stimuli are given, the subject is requested to indicate whether the stimuli were asynchronous or synchronous. If the subject answers correctly, the operator may increase the frequency of the next stimuli to be given. If the subject answers incorrectly, the frequency of the next stimuli is decreased. The frequency may be changed by an approximately constant amount, such as by 26% of the initial frequency.

One of the several threshold finding methods published in psychophysical literature can be used in threshold determination, and different subjects such as children and patients, depending on their capacities, require somewhat different methods. An effective method for normal people is that for all stimuli after the first pair of stimuli, if the subject incorrectly identifies the stimuli type (i.e. synchronous or asynchronous), the frequency is reduced. If the subject correctly identifies the stimuli type, the stimuli are repeated until the subject correctly identifies the type of stimuli four times in a row.

If the subject correctly identifies the type of all four pairs of stimuli, the frequency is increased, and the process continues. In this manner, a single wrong answer by the subject will result in the frequency of the next stimuli being lowered, whereas four correct answers in a row are required to increase the frequency. As the testing continues, and as the subject reaches his threshold for distinguishing between asynchronous and synchronous stimuli, the frequency at which stimuli are generated will be raised and lowered a number of times. As defined herein, an upper turning frequency is the frequency of the stimuli for which a wrong answer was made by the subject after the required number of correct answers (after which the frequency is decreased), and a lower turning frequency is the frequency of the stimuli for which the required number of correct answers as made by the subject for the first time after a wrong answer (after which the frequency is increased).

The subject's overall synchronism threshold can be determined based upon the turning frequencies described above. For example, the overall synchronism threshold could be determined as the average of the fourteen turning frequencies (seven lower and seven upper) following the first two turning frequencies (which are not used in the determination).

FIG. 4 is a circuit diagram of a frequency generating circuit 80 of the testing apparatus 10 that generates a CLOCK signal having a frequency specified by the frequency switches 42, 44. Referring to FIG. 4, the circuit 80 has an oscillator 82, such as a conventional '555 timer integrated circuit, that generates a high-frequency signal on a line 84 connected to a frequency divider 86. The frequency of the signal generated by the oscillator 82 may be varied by turning the switch 44, which is connected to a potentiometer (not shown) that determines the resonant frequency of the oscillator 82. The switch 44 may act to vary the oscillator frequency by a factor of 2.8.

The frequency divider 86, which may be provided in the form of a conventional counter circuit, generates three output signals of varying frequency on three output lines 88, 90, 92. The frequency on the output line 88 may be one-half the frequency of the oscillator signal generated on the line 84; the frequency on the line 90 may be one-fourth the frequency of the oscillator signal; and the frequency on the line 92 may be one-eighth the frequency of the oscillator signal.

The line 88 is provided to a NAND gate 94a along with a select signal on a line 96a; the line 90 is provided to a NAND gate 94b along with a select signal on a line 96b; and the line 92 is provided to a NAND gate 94c along with a select signal on a line 96c.

The select signals on the lines 96 are generated by a logic circuit composed of six NAND gates 100 which are connected, in pairs, to each of three OR gates 102. All of the lines 104 input to the NAND gates 100 are connected to a relatively high voltage, e.g. 5 volts (referred to as logic "1"), via a resistor network 106. The switch 42 has a conductive switch element 42a having a stationary end connected to ground and a rotating end which may be connected to one of the lines 104. The line 104 to which the switch element 42a is connected thus has a relatively low voltage, e.g. 0 volts (referred to as logic "0").

During operation, the one line 104 that has a logic "0" value, due to its being connected to ground via the switch element 42a, will cause the output of the NAND gate 100 to which it is connected to be logic "1," which in turn will cause the OR gate 102 connected to the output of that NAND gate 100 to be logic "1," thus selecting the NAND gate 94 to which the output of the OR gate 102 is provided. With the position of the switch element 42a shown in FIG. 4, the output of the rightmost OR gate 102 will be logic "1," thus selecting the NAND gate 94c, thereby causing the signal provided on the line 92 to be passed to another frequency divider circuit 110.

The frequency divider circuit 110 is composed of three frequency dividers 110a, 110b, 110c, each of which generates an output signal that has a frequency that is a fraction, such as one-tenth, of the frequency of the signal provided to its input.

The signal generated by one of the NAND gates 94 is provided to a NAND gate 112a via a line 114a along with a select signal via a line 116a; the output signal generated by the frequency divider 110a is provided to a NAND gate 112b via a line 114b along with a select signal on a line 116b; the output signal generated by the frequency divider 110b is provided to a NAND gate 112c via a line 114c along with a select signal on a line 116c; and the output signal generated by the frequency divider 110c is provided to a NAND gate 112d via a line 114d along with a select signal on a line 116d.

The select signals on the lines 116 are generated by a logic circuit composed of four NAND gates 120, each of which is connected to three of the lines 104. During operation, the one line 104 that has a logic "0" value, due to its being connected to ground by the switch element 42a, will cause the output of the NAND gate 120 to which it is connected to be logic "1," thus selecting the NAND gate 112 to which the output of the NAND gate 120 is provided. With the position of the switch element 42a shown in FIG. 4, the output of the topmost NAND gate 120 will be logic "1," thus selecting the NAND gate 112a, thereby causing the signal provided on the line 114a to be passed to another frequency divider circuit 130, which further divides the frequency of the signal generated by one of the NAND gates 112, such as by four. The divider 130 generates a CLOCK signal on a line 132, which is used to drive one or more of the stimuli generators 14, 22, 30 as described below.

Figure 5:
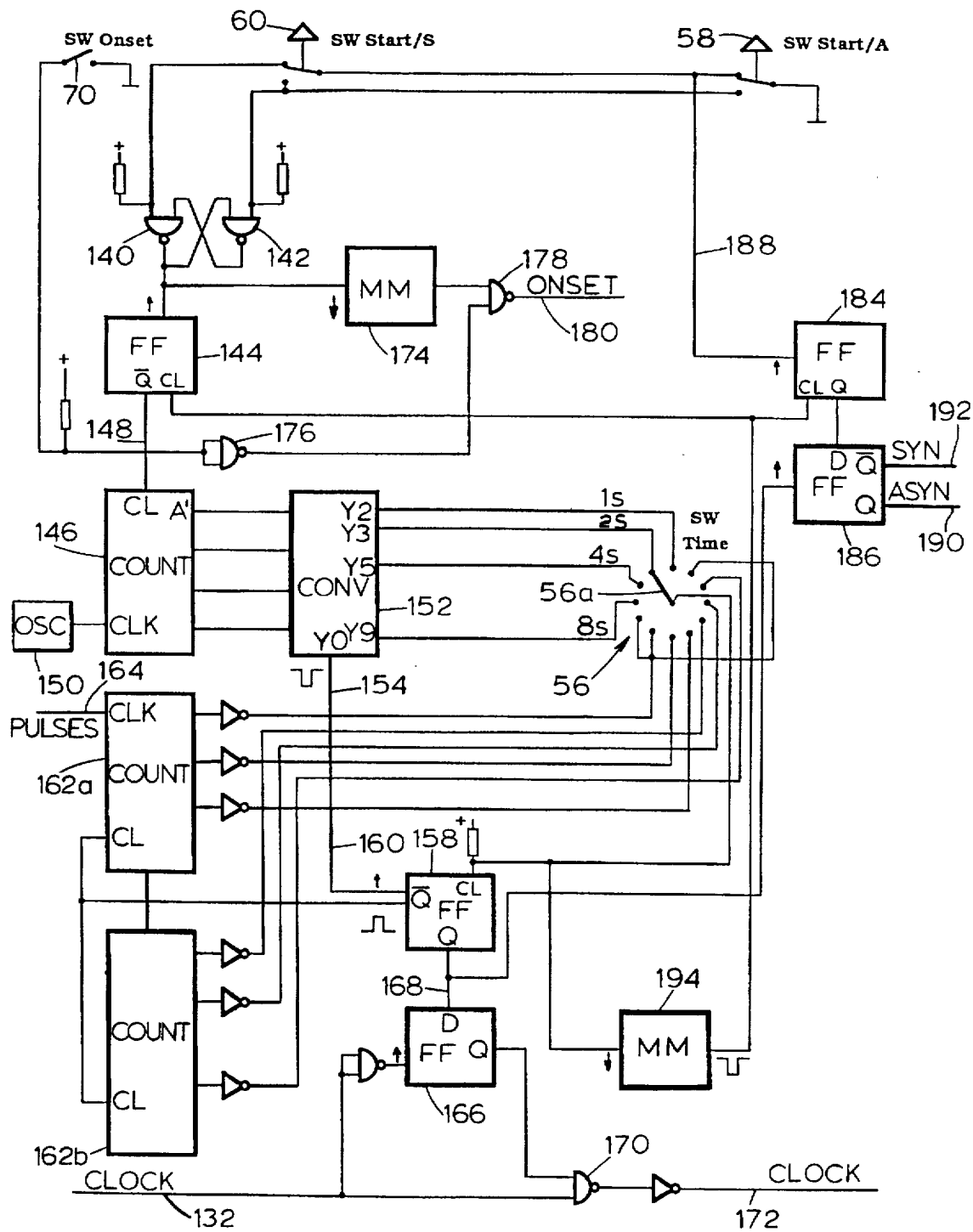
FIG. 5 is a circuit diagram of a first portion of a control circuit of the testing apparatus.

FIG. 5 is a circuit diagram of a first portion of a control circuit of the testing apparatus 10, which controls when the periodic signals that drive the stimuli generators 14, 22, 30, 32 are initiated and how long they last for. Referring to the upper left portion of FIG. 5, when either one of the start buttons 58, 60 is pressed, if the onset switch 70 is closed, a pulse generating circuit in the form of a negative-edge-triggered monostable multivibrator (MM) 174 and a pair of NAND gates 176, 178 generates a single onset mask pulse on a line 180.

When the button 58 or 60 that was pressed by the operator is released, the output generated at the junction of the NAND gates 140, 142 changes from logic "0" to logic "1," triggering a positive-edge-triggered D flip-flop 144 to change its output transmitted to the clear (CL) input of a counter 146 via a line 148. The counter 146 counts the number of pulses of a clock signal generated by an oscillator 150, which may have an oscillation frequency of one hertz. The counter 146 is connected to a conventional BCD-to-decimal converter 152 which converts the binary-coded decimal (BCD) output of the counter 146 into a decimal number, four of which correspond to durations of one, two, four and eight seconds, which may be selected by the switch 56.

Shortly after the counter 146 is cleared by the flip-flop 144, the change in the Y0 output of the converter 152 from logic "0" to logic "1" acts as a "start" signal, which is provided to the positive-edge-triggered input of a flip-flop 158 via a line 160. The start signal causes two actions to take place.

First, the start signal causes the flip-flop 158 to reset to zero a number of counting stages 162a, 162b of a counter 162 which counts the number of pulses of the CLOCK signal (provided to the counter 162 via a line 164) that are used to drive the stimuli generators 14, 22, 30. As described above, the operator may position the time switch 56 to provide a predetermined number of pulses to the stimuli generators 14, 22, 30. Each output line of the counter 162 represents a predetermined number of pulses (e.g. one, two, or four, etc.). When that predetermined number of pulses is reached, that output changes from logic "0" to logic "1," causing a stop signal to be generated (by sending a logic "0" signal to the to the clear input of the flip-flop 158 via a conductive switch element 56a), which stops the CLOCK signal from being provided to the stimuli generators 14, 22, 30.

The Q output of the flip-flop 158 is connected to a flip-flop 166 via a line 168. When the flip-flop 158 receives the start signal, its Q output changes to logic "1," causing the Q output of the flip-flop 166 also to change to logic "1," thus allowing the CLOCK signal on the line 132 to be passed through a NAND gate 170 to a line 172.

When the flip-flop 158 receives a stop signal through the switch element 56a, the Q output of the flip flop 158 changes to logic "0," which causes the Q output of the flip-flop 166 to change to logic "0," thus forcing the output of the NAND gate 170 to be a constant logic "1" and preventing the CLOCK signal from driving the stimuli generators 14, 22, 30.

As noted above, if the switch element 56a is connected to one of the outputs of the counter 162, the counter 162 causes the stop signal to be generated. Alternatively, the switch element 56a could be connected to one of the outputs of the converter 152. In that case, when the counter 146 reaches a count corresponding to the decimal value specified by the switch element 56a, the output of the converter 152 associated with that decimal value changes to logic "0," which causes the flip-flop 158 to be cleared, preventing the CLOCK signal from being passed through the NAND gate 170 as described above.

The asynchronous start button 58 is connected to a D flip-flop 184, which is in turn connected to a second D flip-flop 186. If the asynchronous button 58 is pressed, the signal on an input line 188 changes from logic "0" to logic "1," which causes the Q output of the flip-flop 184 to change to logic "1," which in turn causes the flip-flop 186 to generate an asynchronous select (ASYN) signal having a logic "1" value on a line 190 and a synchronous select (SYN) signal having a logic "0" value on a line 192. If the synchronous start button 60 is pressed, the values of the ASYN and SYN signals on the lines 190, 192 are opposite. The control circuit of FIG. 5A also includes a monostable multivibrator 194 which is used to clear the flip-flops 144, 184 upon the receipt of a stop signal.

FIG. 6 is a circuit diagram of a second portion of the control circuit. Referring to FIG. 6, the CLOCK signal on the line 172 is provided to a pair of monostable multivibrator (MM) circuits 200, 202. Since the MM circuit 200 is triggered by the rising edge of the clock signal (which has a duty cycle of 50%) and the MM circuit 202 is triggered by the falling edge of the CLOCK signal, the two periodic signals output by the MM circuits 200, 202 on a pair of lines 204, 206 are asynchronous, as shown in FIG. 3A.

The periodic signal generated on the line 204 is provided to a driver circuit 210 through an electronic switch 212. The driver circuit 210 amplifies the periodic signal to generate a periodic drive signal that drives the left audio speaker 14. The right speaker 14 is driven by a periodic drive signal generated by a driver circuit 214 connected to an electronic switch 216. If the operator muted the speakers 14 via the mute switch 52 shown in FIG. 1, the electronic switches 212, 216 are opened so that the speakers 14 are not provided with drive signals.

The periodic signal on the line 204 is also provided to an MM circuit 220, the purpose of which is to vary the pulse width (but not the frequency) of the pulses of the periodic signal. The output of the MM circuit 220 is provided to a driver circuit 222 through an electronic switch 224. If the operator did not select the tactile mode of stimulus via the switch 48 (FIG. 1), the electronic switch 224 is opened so that the left sensory solenoid 30 is not provided with a drive signal.

The output of the MM circuit 220 is also provided to drive the left LED 22 (no driver circuit is required since the LEDs 22 require only logic level signals to drive them) through a pair of electronic switches 230, 232. The switch 230 is closed if the operator selected two LEDs for illumination via the switch 54 shown in FIG. 1, and the switch 232 is closed if the operator selected the visual stimulus mode via the switch 50 shown in FIG. 1.

The periodic signal output on the line 206 is provided to an MM circuit 236, which generates an output signal to a logic circuit composed of a NAND gate 238 and an inverter 240. The output of the inverter 240 is provided to a driver circuit 242 through a switch 244 controlled by the tactile sensory select switch 48 as described above.

The NAND gate 238 and the inverter 240 are used to insert a single onset pulse, as described above, in the periodic signal used to drive the left mask solenoid 32. The ONSET signal on the line is also coupled to a NAND gate 250 and a NAND gate 252 to insert onset pulses in the signals which drive the right audio speaker 14 and the right sensory solenoid 30, respectively.

The ASYN and SYN signals on the lines 190, 192 are used to control which of the periodic signals generated on the lines 204, 206 are transmitted to the right sensory solenoid 30, the right LED 22, and the right mask solenoid 32. If the asynchronous start button 58 was pressed, meaning that the selected stimuli generators 14, 22, 30 are to be driven with asynchronous signals, then the ASYN signal on the line 190 will have a value of logic "1" and the SYN signal on the line 192 will have a value of logic "0."

Consequently, when those two signals are provided to a plurality of NAND gates 260, 262, 264, the periodic signal on the line 206 (which is asynchronous to the periodic signal on the line 204) will be passed through the NAND gates 262, 264 to an MM circuit 266 and to a driver circuit 268, through a switch 270 (which is closed if the operator selected the tactile mode of stimulation via the switch 48), to generate a periodic drive signal to drive the right sensory solenoid 30. The output of the MM circuit 266 is also used to drive the right LED 22 through a switch 272 (which is closed if the operator selected the visual mode of stimulation via the switch 50).

It should also be noted that if the asynchronous start button 58 was pressed, the right audio speaker 14 will be driven asynchronously from the left audio speaker 14 (due to the periodic signal on the line 206 being passed through the NAND gates 264 and 250 to the driver 214).

When the ASYN and SYN signals have opposite values (when the synchronous start button 60 was pressed), the periodic signal on the line 204 is transmitted to the MM circuit 266 so that both the right and left sensory solenoids 30 are driven synchronously from the same periodic signal.

A logic circuit composed of three NAND gates 276, 278, 280 ensures that the right mask solenoid 32 is always driven asynchronously with the right sensory solenoid 30, through an MM circuit 282, a switch 284, and a driver circuit 286. The driver circuits 222, 242, 268, 286 used to drive the solenoids 30, 32 can be composed of two-stage transistor circuits, and the driver circuits 210, 214 for the audio speakers 14 can be single stage transistor circuits.

Figure 7:
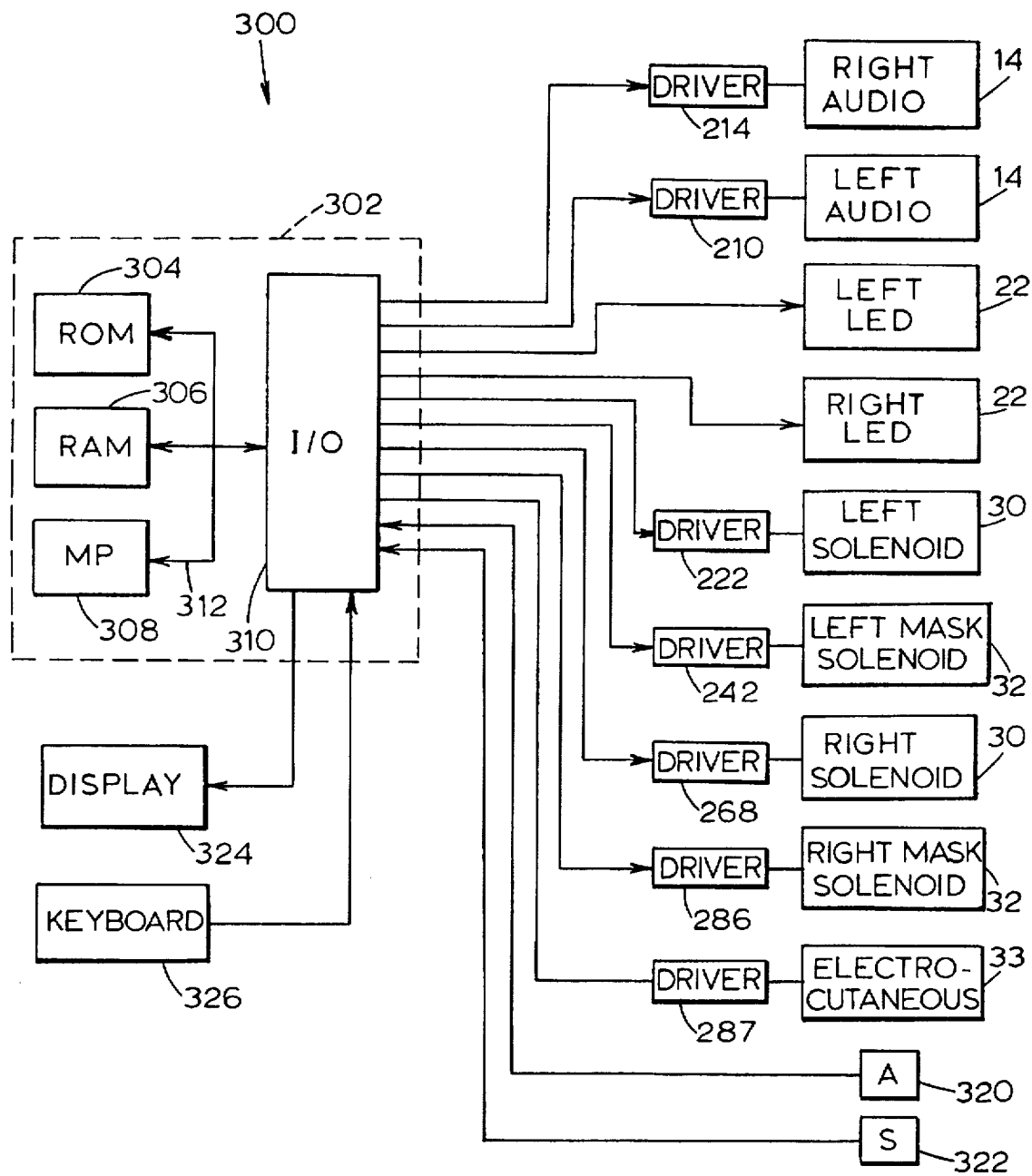
FIG. 7 is a block diagram of a second embodiment of a testing apparatus in accordance with the invention.

A second embodiment of a testing apparatus 300 which incorporates a controller of the type used in a personal computer is illustrated in FIG. 7. Referring to FIG. 7, the testing apparatus 300 has a controller 302 which is composed of a read-only memory (ROM) 304, a random-access memory (RAM) 306, a microprocessor (MP) 308 and an input/output (I/O) circuit 310, all of which are interconnected via an address/data bus 312. An electrocutaneous stimulator 33 with driver 287 may be used to deliver electrical stimuli. This output device adds to the possibilities of intermodal stimulation explained above tactile/electrocutaneous, visual/electrocutaneous, and auditory/electrocutaneous stimulation.

The I/O circuit 310 is connected to drive the seven stimulus generators 14, 22, 30, 33 and the two mask solenoids 32 described above. The I/O circuit 310 is also connected to receive signals from an asynchronous pushbutton 320 and a synchronous pushbutton 322, one of which may be pressed by the subject being tested to indicate whether the subject believes that the stimuli just given were asynchronous or synchronous, respectively. The testing procedure may be controlled by the operator through a display device 324, such as a cathode ray tube or other output device, and a keyboard 326 or other input device, such as an electronic mouse or a disk.

The I/O circuit 310 may generate any combination of synchronous and asynchronous periodic signals of the type shown in FIGS. 3A and 3B to the stimuli generators 14, 22, 30, 33, depending upon the instructions given by the operator to the controller 302 via the keyboard 326. The operator may instruct the controller 302 to transmit $\Psi$, by means of a random number generator, pairs of asynchronous or synchronous periodic signals to one or more pairs of the stimulus generators. Alternatively, the operator may instruct the controller 302 to transmit a first periodic signal to one type of stimulus generator, such as one of the LEDs 14, and a second periodic signal to a different type of stimulus generator, such as one of the solenoids 22, the first and second signals being either synchronous or asynchronous at random.

Figure 8A:
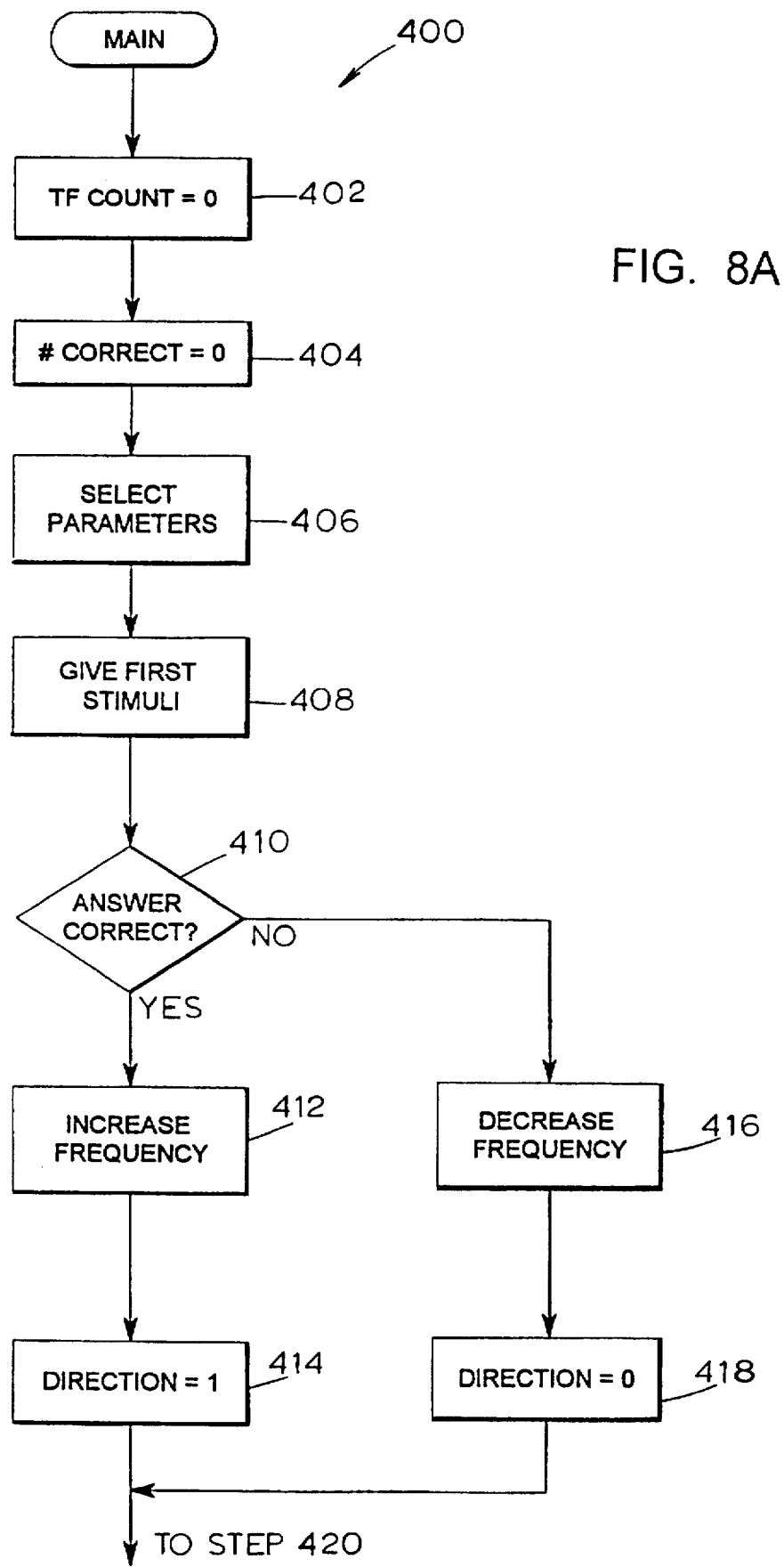
FIGS. 8A and 8B are flowcharts illustrating the operation of the testing apparatus of FIG. 7.

The operation of the testing apparatus 300 is described below in connection with FIGS. 8A and 8B, which illustrate a flowchart of a computer program 400 stored in the devices ROM 304 and RAM 306, and executed by the microprocessor 308. Referring to FIG. 8A, the program 400 begins operation at step 402 where a TFCOUNT variable, which represents the number of turning frequencies during the testing period, is set to zero. As described above, a turning frequency is the frequency at which the direction of frequency adjustment changed, e.g. from increasing to decreasing, from one pair of stimuli to a subsequent pair of stimuli. At step 404, a #CORRECT variable, which represents the number of correct answers in a row made by the subject, is set to zero.

At step 406, the parameters of the threshold search and of the stimuli to be given during a test sequence are selected by the operator. As described above, these parameters include the number of turning frequencies if it is other than a default value, the type of stimuli, the duration of the stimuli, the initial frequency of the stimuli, the nature of the feedback given to the subject after responses, and the nature of masking stimuli used (a computer program allows many possibilities of masking). At step 408, a first pair of stimuli, synchronous or asynchronous pair generated at random, are presented to the subject by sending periodic signals to the stimuli generators 14, 22, 30, 33 selected by the operator at step 406; the stimulus pair is presented when the subject presses either one of the response buttons 320 or 322.

After receiving the stimuli, the subject indicates whether the stimuli were synchronous or asynchronous by pressing one of the buttons 320, 322. At step 410, if the button pressed by the subject correctly identifies the nature of the stimuli given at step 408, the program branches to step 412, where the frequency at which the next stimuli will be given is increased, e.g. by a constant amount. At step 414, a DIRECTION flag is set to one to indicate that the frequency is currently changing in the increasing direction during the test sequence.

At step 410, if the subject did not press the correct one of the buttons 320, 322, the program branches to step 416 where the frequency at which the next stimuli will be given is decreased. At step 418, the DIRECTION flag is set to zero to indicate that the frequency is currently changing in the decreasing direction.

Figure 8B:
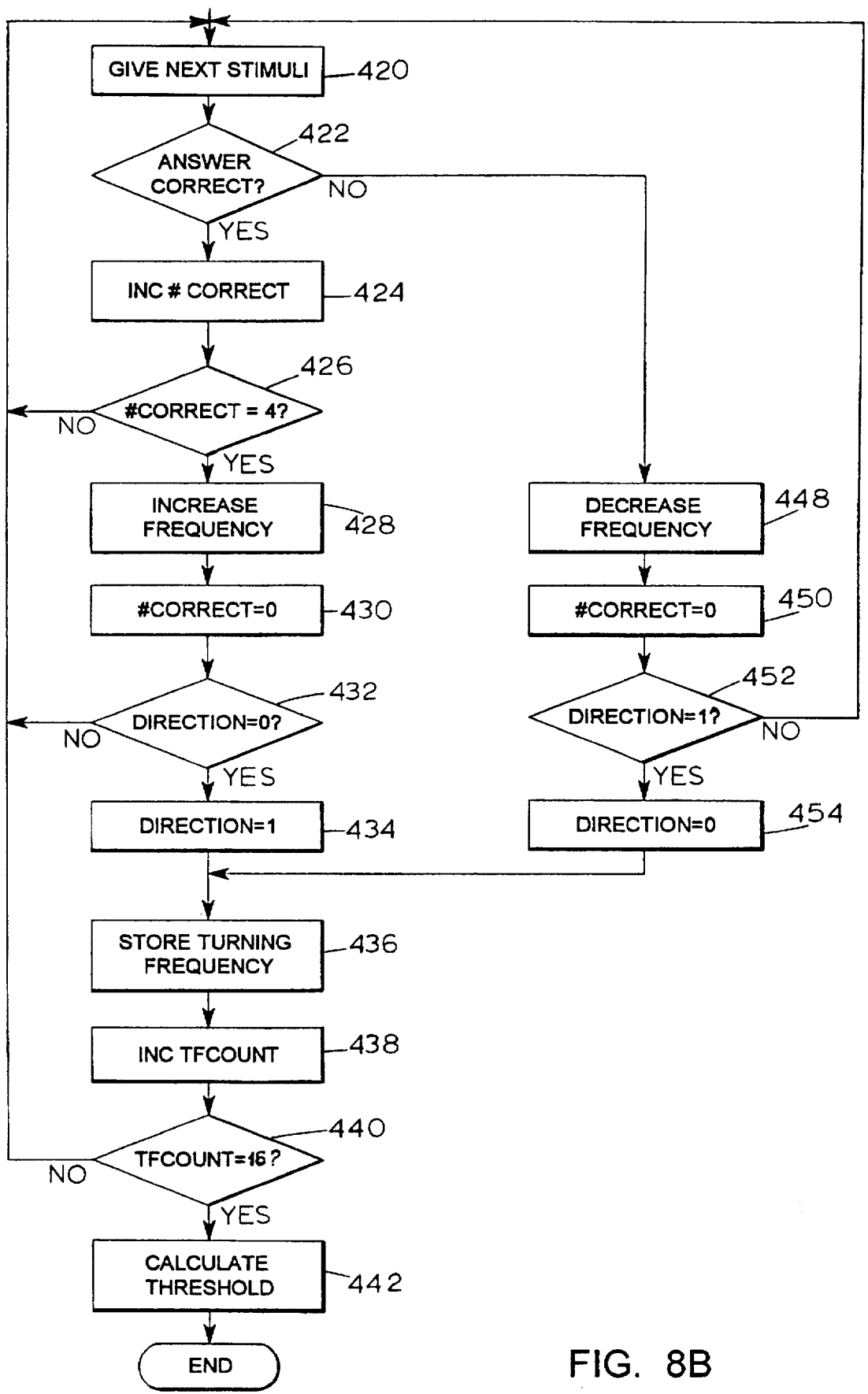

Referring to FIG. 8B, at step 420 the next stimuli is given to the subject at the new frequency specified at one of steps 412, 416. At step 422, if the subject correctly identifies whether the stimuli are synchronous or asynchronous, the program branches to step 424, where the #CORRECT variable is incremented by one. At step 426, if the value of the #CORRECT variable is equal to four (or another preselected number), meaning that the subject has made four correct answers in a row, the program branches to step 428, where the frequency at which the next stimuli will be given is increased. At step 430, the value of the #CORRECT variable is reset to zero since the frequency has just been increased and since the subject needs to make four correct answers in a row before the frequency will be increased again. If the #CORRECT variable is not equal to four as determined at step 426, the program branches back to step 420 where the next stimuli are given at the same frequency as the previous stimuli.

At step 432, if the DIRECTION flag is zero, meaning that the previous direction in which the frequency was changing was the decreasing direction, then the program branches to step 434 where the DIRECTION flag is set to one. If the program reaches step 434, then the direction has just changed, meaning that the frequency at which the previous stimuli was given constitutes a turning frequency. Accordingly, at step 436, the turning frequency is stored in the RAM 306, and at step 438 the TFCOUNT variable is incremented by one since another turning frequency has just been stored.

If the DIRECTION flag is not equal to zero as determined at step 432, the program branches back to step 420, where the next stimuli are given to the subject at the new frequency specified at step 428.

At step 440, if the value of the TFCOUNT variable is 16 (or another predetermined number), meaning that there are 16 turning frequencies stored in memory, the program branches to step 442, where the subject's synchronism threshold is determined based upon the values of the stored turning frequencies and the result is stored.

As described above, one way of calculating this threshold would be to determine the average of the fourteen turning frequencies (seven lower and seven upper) following the first two turning frequencies (which are not used in the determination). Other ways of determining the subject's overall synchronism threshold could be used.

If the number of turning frequencies stored in memory is less than 16 as determined at step 440, the program branches back to step 420, where the next stimuli are given to the subject at the new frequency specified at one of steps 428 or 448.

If at step 422 the subject answered incorrectly, the program branches to step 448, where the frequency at which the next stimuli will be given is decreased. At step 450, the value of the #CORRECT variable is reset to zero (in case the subject made one or more correct answers before giving the incorrect answer).

At step 452, if the DIRECTION flag is one, meaning that the previous direction in which the frequency was changing was the increasing direction, then the program branches to step 454 where the DIRECTION flag is set to zero. If the program reaches step 454, then the direction has just changed, meaning that the frequency at which the previous stimuli was given constitutes a turning frequency. In that case, the program branches to step 436, where the new turning frequency is stored in memory, and the program continues operation as described above.

In one manner of testing, a particular input function of the brain may be tested as described below. The subject is first given a predetermined number of stimulus pairs, such as eight pairs, via one of the stimuli generators 14, 22, 30, 33, in which the probability of an asynchronous stimuli pair is 50%.

After the initial series is given, when the subject believes that the overall probability of receiving an asynchronous stimulus pair is 50%, the subject is given a number of series of stimulus pairs in which the probability of an asynchronous pair within each series is either 15% or 85% (e.g. a first series of eight stimulus pairs in which the probability of an asynchronous pair is 15%, then a second series of eight stimulus pairs in which the probability of an asynchronous pair is 85%). Whether the probability of an asynchronous pair in each series is 15% or 85% can be determined randomly, e.g. a 50% chance of being 15% and a 50% chance of being 85%.

During this testing, the subject is given no feedback regarding the correctness of the responses, so that this testing method reduces the likelihood of correct answers being generated by guessing or other irrelevant cues, such as any audible difference between the synchronous and asynchronous stimuli. This testing method could be implemented in the computer program 400, or it could be implemented manually by the operator of the first embodiment of the testing apparatus 10.

The tactile stimulation described above could be generated by means other than the solenoids 30, 32. For example, conventional piezoelectric elements could be used to generate the tactile stimulation.

Additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A method of exposing a subject to periodic stimuli in order to assess the working quality of the brain of the subject, said method comprising the steps of:
   (a) exposing the subject to a first periodic stimulus having a substantially constant frequency during a first period of time;
   (b) exposing the subject to a second periodic stimulus having a substantially constant frequency during said first period of time while the subject is being exposed to said first periodic stimulus, said frequency of said second periodic stimulus being substantially the same as said frequency of said first periodic stimulus;
   (c) receiving form the subject an indication whether said first and second periodic stimuli are synchronous or asynchronous;
   (d) depending on the accuracy of said indication given by the subject, selecting a new substantially constant frequency, said new frequency being different than said frequency of said first and second periodic stimuli;
   (e) exposing the subject to a third periodic stimulus having said new frequency during a second period of time; and
   (f) exposing the subject to a fourth periodic stimulus having said new frequency during said second period of time while the subject is being exposed to said third periodic stimulus.

2. A method as defined in claim 1 wherein said step (d) comprises the step of increasing the frequency at which subsequent periodic stimuli are generated in response to a predetermined number of correct indications given by the subject.

3. A method as defined in claim 1 wherein said step (d) comprises the step of decreasing the frequency at which subsequent periodic stimuli are generated in response to an incorrect indication given by the subject.

4. A method as defined in claim 1 wherein said steps (c) through (f) are repeated until said periodic stimuli exhibit a predetermined number of turning frequencies, each of said turning frequencies representing a frequency at which there was a directional frequency change.

5. A method as defined in claim 4 additionally comprising the step of calculating a synchronism threshold of the subject based upon said turning frequencies.

6. A method as defined in claim 4 additionally comprising the step of calculating a synchronism threshold of the subject by determining an average of a predetermined number of said turning frequencies.

7. A method as defined in claim 1 wherein said step (b) comprises the step of exposing the subject to a second periodic stimulus that is synchronous with said first periodic stimulus.

8. A method as defined in claim 7 wherein said step (f) comprises the step of exposing the subject to a fourth periodic stimulus that is synchronous with said third periodic stimulus.

9. A method as defined in claim 1 wherein said step (b) comprises the step of exposing the subject to a second periodic stimulus that is asynchronous with said first periodic stimulus.

10. A method as defined in claim 9 wherein said step (f) comprises the step of exposing the subject to a second periodic stimulus that is synchronous with said first periodic stimulus.

11. A method as defined in claim 1 wherein each of said steps (a), (b), (e) and (f) comprises the step of exposing the subject to a visual periodic stimulus.

12. A method as defined in claim 1 wherein each of said steps (a), (b), (e) and (f) comprises the step of exposing the subject to a tactile periodic stimulus.

13. A method of exposing a subject to periodic stimuli in order to asses the working quality of the brain of the subject, said method comprising the step of;
   (a) exposing the subject to a first periodic stimulus having a substantially constant frequency during a first period of time;
   (b) exposing a subject to a second periodic stimulus having a substantially constant frequency during a first period of time while the subject is being exposed to said first periodic stimulus, said frequency of periodic stimulus being substantially the same as said frequency of said first periodic stimulus;
   (c) receiving from the subject in indication whether said first and second periodic stimuli are synchronous or asynchronous;
   (d) selecting a new substantially constant frequency substantially different than said frequency of said first and second periodic stimuli;
   (e) exposing a subject to a third periodic stimulus having said new frequency during a second period of time; and (f) exposing the subject to a fourth periodic stimulus having said new frequency during said second periodic of time while the subject is being exposed to said periodic stimulus.

14. A method as defined in claim 13 wherein said step (b) comprises the step of exposing the subject to a second periodic stimulus that is synchronous with said first periodic stimulus and wherein said step (f) comprises the step of exposing the subject to a fourth periodic stimulus that is asynchronous with said third periodic stimulus.

15. A method as defined in claim 13 wherein said step (a) comprises the step of exposing the subject to a first type of periodic stimulus and wherein said step (b) comprises the step of exposing the subject to a second type of periodic stimulus.

16. A method as defined in claim 15 wherein said step (a) comprises the step of exposing the subject to a visual periodic stimulus and wherein said step (b) comprises the step of exposing the subject to a tactile periodic stimulus.

17. An apparatus for generating periodic stimuli to enable the assessment of the working quality of the brain, said apparatus comprising:

first stimuli-generating means for generating periodic stimuli to a subject during a testing sequence;

second stimuli-generating means for generating means for generating periodic stimuli to the subject during the testing sequences;

means for generating a first periodic signal having a substantially constant frequency and transmitting said first periodic signal to said first stimuli-generating means;

means for generating a second periodic signal having a substantially constant frequency substantially equal to said frequency of said first periodic signal and transmitting said second periodic signal to said second stimuli-generating means;

switch means for selecting whether said first and second periodic signal are synchronous or asynchronous; and means for adjusting the frequency at which said first and second periodic signals are generated.

18. An apparatus as defined in claim 17 wherein each of said first and second stimuli-generating means comprises means for generating visual stimuli.

19. An apparatus as defined in claim 17 wherein each of said first and second stimuli-generating means comprises means for generating tactile stimuli.

20. An apparatus as defined in claim 17 additionally comprising third and fourth stimuli-generating means for generating periodic stimuli to the subject during the testing sequence, said first and second stimuli-generating means comprising means for generating a first type of stimuli and said third and fourth stimuli-generating means comprising means for generating a second type of stimuli.

21. An apparatus as defined in claim 20 wherein each of said first and second stimuli-generating means comprises means for generating visual stimuli and wherein each of said third and fourth stimuli-generating means comprises means for generating tactile stimuli.

22. An apparatus as defined in claim 17 wherein said frequency-adjusting means comprises at least one switch for manually changing the frequency at which said first and second periodic signals are generated.

23. An apparatus as defined in claim 17 wherein said switch means comprises an asynchronous-stimulus start pushbutton and a synchronous-stimulus start pushbutton.

24. An apparatus for generating periodic stimuli to enable the assessment of the working quality of the brain, said apparatus comprising:

first stimuli-generating means for generating periodic stimuli to a subject during a testing sequence;

second stimuli-generating means for generating periodic stimuli to the subject during the testing sequence;

means for generating a first periodic signal having a substantially constant frequency and transmitting said first periodic signal to said first stimuli-generating means;

means for generating a second periodic signal having a substantially constant frequency substantially equal to said frequency of said first periodic signal and transmitting said second periodic signal to said second stimuli-generating means;

switch means for selecting whether said first and second periodic signals are synchronous or asynchronous;

means for adjusting the frequency at which said first and second periodic signals are generated; and indicating means for allowing the subject to make an indication as to whether said first and second periodic stimuli were synchronous or asynchronous.

25. An apparatus as defined in claim 24 wherein said indicating means comprise a first pushbutton and a second pushbutton.

26. An apparatus as defined in claim 24 additionally comprising means for calculating a synchronism threshold of the subject based upon a plurality of indications made by the subject via said indicating means.

27. An apparatus as defined in claim 24 wherein said frequency-adjusting means comprises means for automatically increasing the frequency at which said first and second periodic signals are generated in response to a predetermined number of correct indications made by the subject via said indicating means.

28. An apparatus as defined in claim 24 wherein said frequency-adjusting means comprises means for automatically decreasing the frequency at which said first and second periodic signals are generated in response to a predetermined number of correct indications made by the subject via said indicating means.

* * * * *